United States Patent [19]

Crissman et al.

[11] Patent Number: 5,185,260
[45] Date of Patent: Feb. 9, 1993

[54] METHOD FOR DISTINGUISHING NORMAL AND TRANSFORMED CELLS USING G1 KINASE INHIBITORS

[75] Inventors: Harry A. Crissman; Donna M. Gadbois; Robert A. Tobey, all of Los Alamos; E. Morton Bradbury, Santa Fe, all of N. Mex.

[73] Assignee: The United States of America as represented by the United States Department of Energy, Washington, D.C.

[21] Appl. No.: 751,855

[22] Filed: Aug. 29, 1991

[51] Int. Cl.$^5$ ............................................. C12N 1/38
[52] U.S. Cl. ............................. 435/244; 435/252.3; 435/240.1; 424/573; 536/18.7; 540/545
[58] Field of Search ................. 536/24, 22, 18.2, 18.7; 435/252.3, 244, 240.1; 424/573; 540/545

[56] References Cited

U.S. PATENT DOCUMENTS 4,877,776 10/1989 Murakata et al. ................ 536/24

OTHER PUBLICATIONS

Kiyoto, Itsumi et al., "Staurosporine"... in *Biochem. and Biophys. Res. Comm.*, 148:2, pp. 740-746, 1987.
Calabretta, Bruno et al., "Expression of c-myc...," *Cancer Research*, vol. 45, pp. 6000-6004, 1985.

Primary Examiner—Ronald W. Griffin
Assistant Examiner—Pamela S. Webber
Attorney, Agent, or Firm—Ray G. Wilson; Paul D. Gaetjens; William R. Moser

[57] ABSTRACT

A $G_1$ phase kinase inhibitor is applied in a low concentration to a population of normal and transformed mammalian cells. The concentration of $G_1$ phase kinase inhibitor is selected to reversibly arrest normal mammalian cells in the $G_1$ cell cycle without arresting growth of transformed cells. The transformed cells may then be selectively identified and/or cloned for research or diagnostic purposes. The transformed cells may also be selectively killed by therapeutic agents that do not affect normal cells in the $G_1$ phase, suggesting that such $G_1$ phase kinase inhibitors may form an effective adjuvant for use with chemotherapeutic agents in cancer therapy for optimizing the killing dose of chemotherapeutic agents while minimizing undesirable side effects on normal cells.

7 Claims, 6 Drawing Sheets

KT252b Treatment
DNA Content

KT5720 Treatment
DNA Content

KT5823 Treatment
DNA Content

KT5926 Treatment
DNA Content

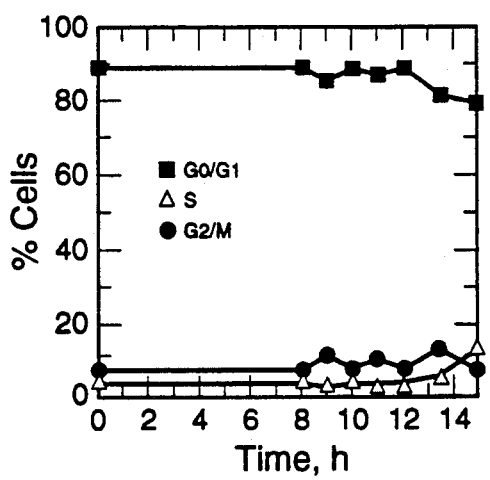
Fig. 4A Low Serum
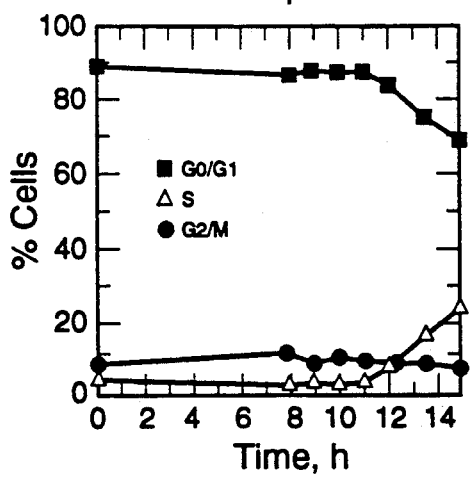
Fig. 4B Stsp
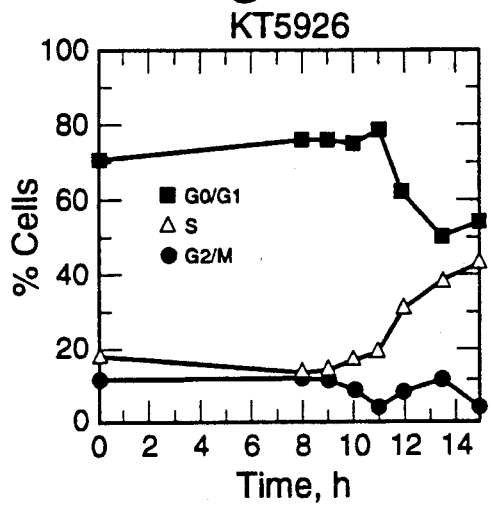
Fig. 4C KT5926
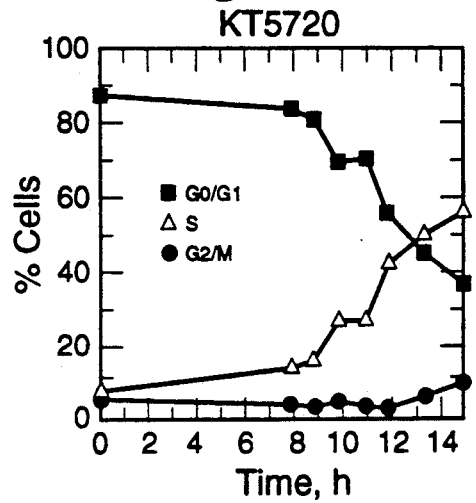
Fig. 4D KT5720
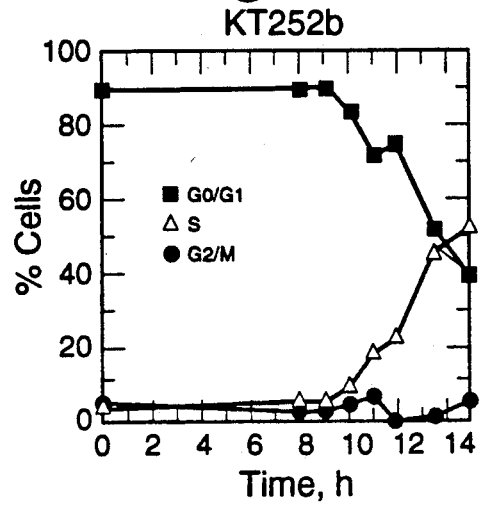
Fig. 4E KT252b
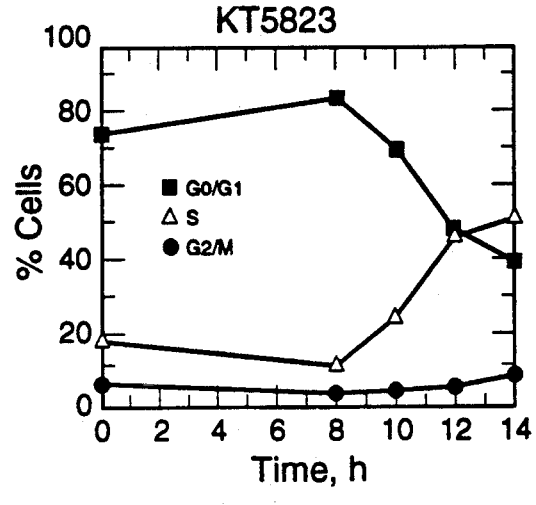
Fig. 4F KT5823

METHOD FOR DISTINGUISHING NORMAL AND TRANSFORMED CELLS USING G1 KINASE INHIBITORS

This invention is the result of a contract with the Department of Energy (Contract No. W-7405-ENG-36).

BACKGROUND OF INVENTION

This invention relates to cancer research and treatment and, more particularly, to methods for distinguishing normal, neoplastic, and transformed, i.e., tumor, cells for observation and selective treatment.

There are many needs in cancer research, diagnosis, and treatment to distinguish normal, neoplastic, and transformed cells. As used herein, the term "transformed cells" means cells that are undergoing or have undergone neoplastic transformation. In research it would be useful to determine the onset of cell transformation; e.g., rodent cells can undergo a spontaneous transformation and it would be highly desirable to verify that a particular culture is free of transformed cells at the beginning of an experiment. Research needs also require that transformed cell lines be developed and characterized for investigation. The development of such cell lines would be enhanced if the growth of normal cells could be suppressed to allow the outgrowth of transformed cells. Likewise, patient tissue assays may contain only a few transformed cells within the population of normal cells. The transformed cells are difficult to distinguish from the normal cells using conventional techniques. In accordance with the present invention, transformed cells can be caused to have preferential growth over normal cells so that the presence of a small number of transformed cells can be determined by subsequent large colonies.

In cancer chemotherapy, chemotherapeutic agents are used to kill transformed cells. However, the chemical agents also kill normal cycling cells and create highly undesirable side effects. In accordance with another aspect of the present invention, normal cells may be arrested in $G_1$ phase of the cell cycle and thus protected from the effects of a selected therapeutic agent that kills the cycling cancer cells. In this case the therapy regimen may be designed for optimum killing of transformed cells.

Accordingly, it is an object of the present invention to provide a process for arresting the growth of normal cells without affecting the growth of transformed cells.

It is another object of the present invention to reversibly arrest the growth of normal cells without affecting the growth of transformed cells.

Yet another object is to reversibly arrest the growth of normal cells in $G_1$ phase of the cell cycle so that they are protected from the effects of chemotherapeutic agents directed to killing the cycling transformed cells.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method of this invention involves treating a population of normal and transformed mammalian cells with a low concentration of a $G_1$ phase kinase inhibitor which reversibly arrests normal mammalian cells in the $G_1$ cell cycle stage without arresting the growth of transformed cells.

In a preferred embodiment, the kinase inhibitor is staurosporine and the concentration is in the range 1–10 ng/ml. In addition, other kinase inhibitors have been found that have the same effect as staurosporine.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIGS. 4A, B, C, D, E, and F graphically depict the recovery kinetics of the HSF55 cells from a serum-deprived arrest and kinase-inhibited $G_1$ states.

DETAILED DESCRIPTION OF THE INVENTION

Figure 1:
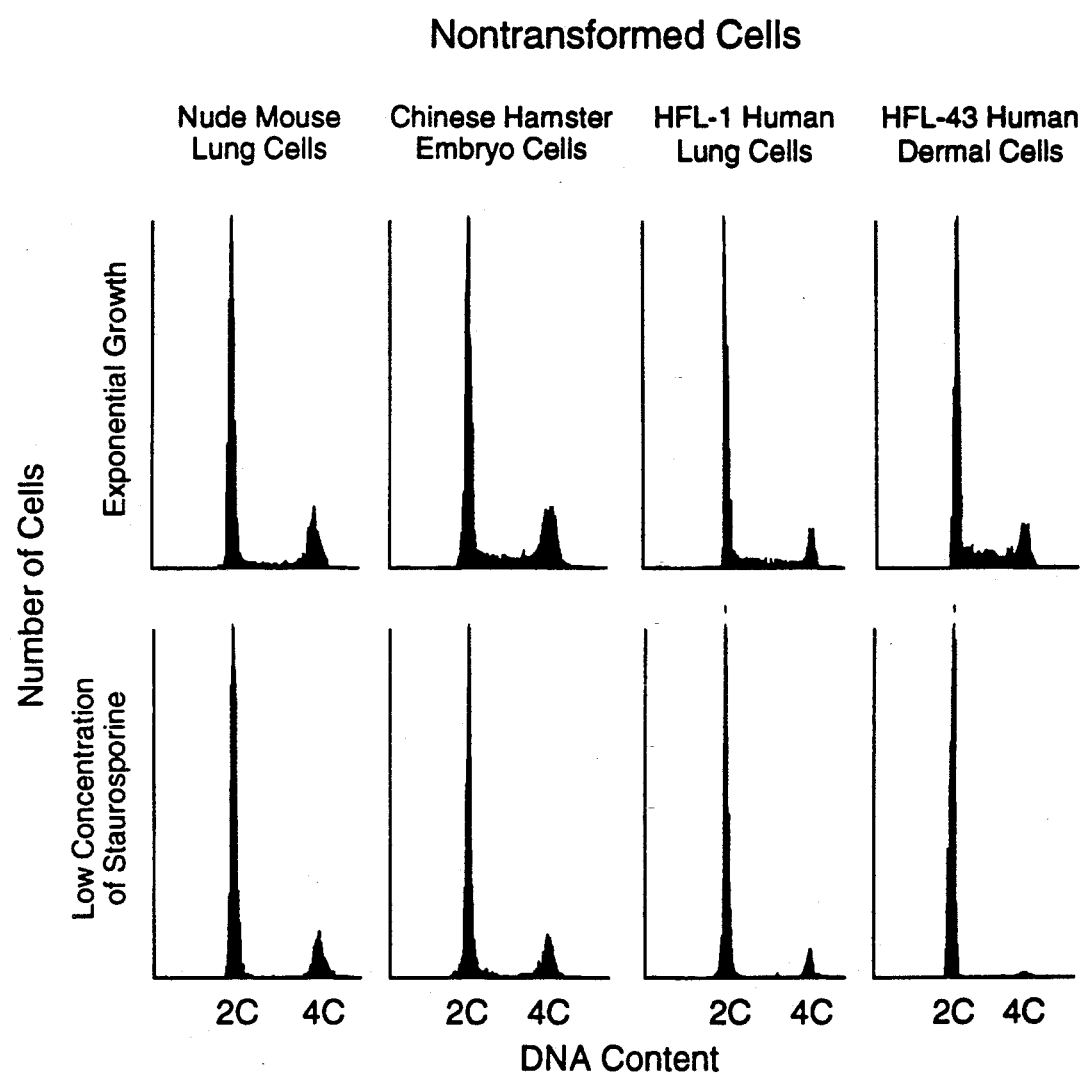
FIGS. 1A and 1B graphically depict the effect of the kinase inhibitor staurosporine on the growth of normal and transformed mammalian cells.

In accordance with the present invention, transformed mammalian cells are distinguished from normal mammalian cells by treating the cells with a low concentration of a $G_1$ phase kinase inhibitor, such as staurosporine. Whereas the low concentrations reversibly prevent the normal cells from entering S-phase of the cell cycle, growth cycle of the transformed cells is not affected. Thus, in the presence of the $G_1$ phase kinase inhibitor, transformed cells continue to cycle whereas normal cells are blocked and this finding is the basis for applications to research, diagnostic, and treatment procedures. In the presence of the $G_1$ phase kinase inhibitor populations of normal and transformed cells may be treated with a chemotherapeutic agent that will selectively kill the cycling transformed cells. After the chemotherapeutic treatment, the kinase inhibitor may be removed to return the normal cells to the cell growth cycle.

In one embodiment of the present invention, levels of staurosporine as low as 1 ng/ml prevented normal cells from entering S phase (i.e., induced $G_1$ arrest). At higher concentrations of staurosporine (50–75 ng/ml), normal mammalian cells are arrested in both $G_1$ and $G_2$. The period of sensitivity of normal human diploid fibroblasts to low levels of staurosporine commenced 3 hr later than the $G_0/G_1$ boundary and extended through the $G_1S$ boundary.

Interference with activity of the $G_1$-essential kinase(s) caused normal human cells traversing mid-to-late $G_1$ at the time of staurosporine addition to be "set back" to the initial staurosporine block point, suggesting the existence of a kinase-dependent "$G_1$ clock" mechanism that must function continuously throughout the early cycle in normal cells. In contrast to the behavior of normal cells, neither low nor high concentrations of staurosporine affected $G_1$ progression in transformed cells. These results show that kinase-mediated processes are essential both for cell progression through most of $G_1$ and for initiation of DNA synthesis, but only in normal mammalian cells. Staurosporine was without effect on $G_1$ progression and initiation of genome replication in transformed cells. Other $G_1$ phase kinase inhibitors have also been found to reversibly arrest normal cells but not transformed cells, in $G_1$ phase of the cell cycle.

METHODS AND MATERIALS

Nontransformed Cells

Human diploid fibroblasts strains 43 (HSF43)(Ray et al., 42 J. Cell. Biochem., pp. 13-31 (1990)) and 55 (HSF55)(Tobey et al., 87 Proc. Natl. Acad. Sci. USA, pp. 5104-5108 (1990)) were derived from neonatal foreskin samples and cultured in alpha minimum essential medium containing 10% bovine calf serum ($\alpha$MEM/10% BCS). HFL-1 diploid fibroblasts (Tobey et al., 16 Exp. Lung Res., pp. 235-255 (1990)) were obtained from the American Type Culture Collection and maintained in $\alpha$MEM supplemented with 10% bovine fetal serum ($\alpha$MEM/10% BFS). Human cells from passages 9 to 14 were used in these studies. Early-passage (passages 3-5) cells initiated from a Chinese hamster embryo (Kraemer et al., 43 Cancer Res., pp. 4822-4827 (1983)) were grown in $\alpha$MEM/10% BFS. Fibroblasts (passage 3) isolated from the lungs of adult athymic BALB/c (nude) mice (Harlan-Sprague-Dawley), as described previously for isolation of rat lung fibroblasts (Tobey et al., 16 Exp. Lung Res., pp. 235-255 (1990)), were grown in $\alpha$MEM/10% BFS.

Transformed Cells

The FT210 mouse mammary carcinoma line (Mineo et al., 167 Exp. Cell Res., pp. 53-62 (1986)) was provided by Masa-atsu Yamada (Faculty of Pharmaceutical Sciences, University of Tokyo) and Hideyo Yasuda (Faculty of Pharmaceutical Science, Kanazawa University); the cells were grown at 32° C. in RPMI-1640/10% BFS. The tumorigenic WCHE/5 clone 23 T3 Chinese Hamster cells (Bartholdi et al., 13 Somatic Cell Mol. Genet., pp. 1-10 (1987)) were grown in $\alpha$MEM/10% BFS. HL-60 human leukemia cells (Collins, et al., 260 Nature (London), pp. 347-349 (1977)) were maintained in RPMI/10% BFS. The CT10-2C-T1 cell line (Ray et al., 42 J. Cell. Biochem., pp. 13-31 (1990)) was obtained by introducing into nontransformed HSF-43 human diploid fibroblasts a plasmid containing the gene for the simian virus 40 large tumor (T) antigen linked to a Rous sarcoma virus promoter. The resultant CT10-2C-TI transformed cells were recovered from rapidly growing tumors in nude mice (id.) and grown in $\alpha$MEM/10% BCS.

Flow Cytometric Measurements and Preparation of Stock Solutions

For determination of DNA distributions, mithramycin-stained cells were analyzed in a flow cytometer at 457 nm (Tobey et al., 179 Exp. Cell Res., pp. 400-416 (1988)). The 5-bromodeoxyuridine (BrdUrd)-flow cytometric procedure (Crissman et al., 173 Exp. Cell Res., pp. 256-261 (1987)) was used to distinguish between noncycling and cycling $G_1$ cells. Stock solutions of staurosporine (Kamiya Biomedical Company, Thousand Oaks, Calif.) and BrdUrd (Sigma) were prepared in dimethyl sulfoxide and water, respectively. The amount of dimethyl sulfoxide added to cell cultures was $\leq 0.1\%$ (vol/vol) and did not affect cell growth rate.

RESULTS

Effect of Staurosporine on Nontransformed Cells (FIG. 1A)

Experiments were carried out with cultures of early-passage, nontransformed cells that were treated with various concentrations of staurosporine. When normal cells were treated with low concentrations of staurosporine, ranging from 1 to 10 ng/ml (2.2-22 nM) for periods of time approximating the culture doubling time, there was an emptying of S, $G_2$(4C), and M phases and accumulation of cells with a 2C ($G_0/G_1$) DNA content. The cultures were maintained at $<3 \times 10^6$ cells per 75-cm$^2$ flask to preclude confluency inhibition of growth. FIG. 1A graphically depicts the number of normal mammalian cells with 2C ($G_1$) and 4C ($G_2$) DNA content during a normal exponential growth cycle and after treatment with 1-10 ng/ml staurosporine. Normal cell samples were taken of nude mouse lung cells, Chinese hamster embryo cells, human lung cells, and human dermal cells. In all cases, treatment with staurosporine arrested cell growth in $G_0/G_1$.

Figure 1B:
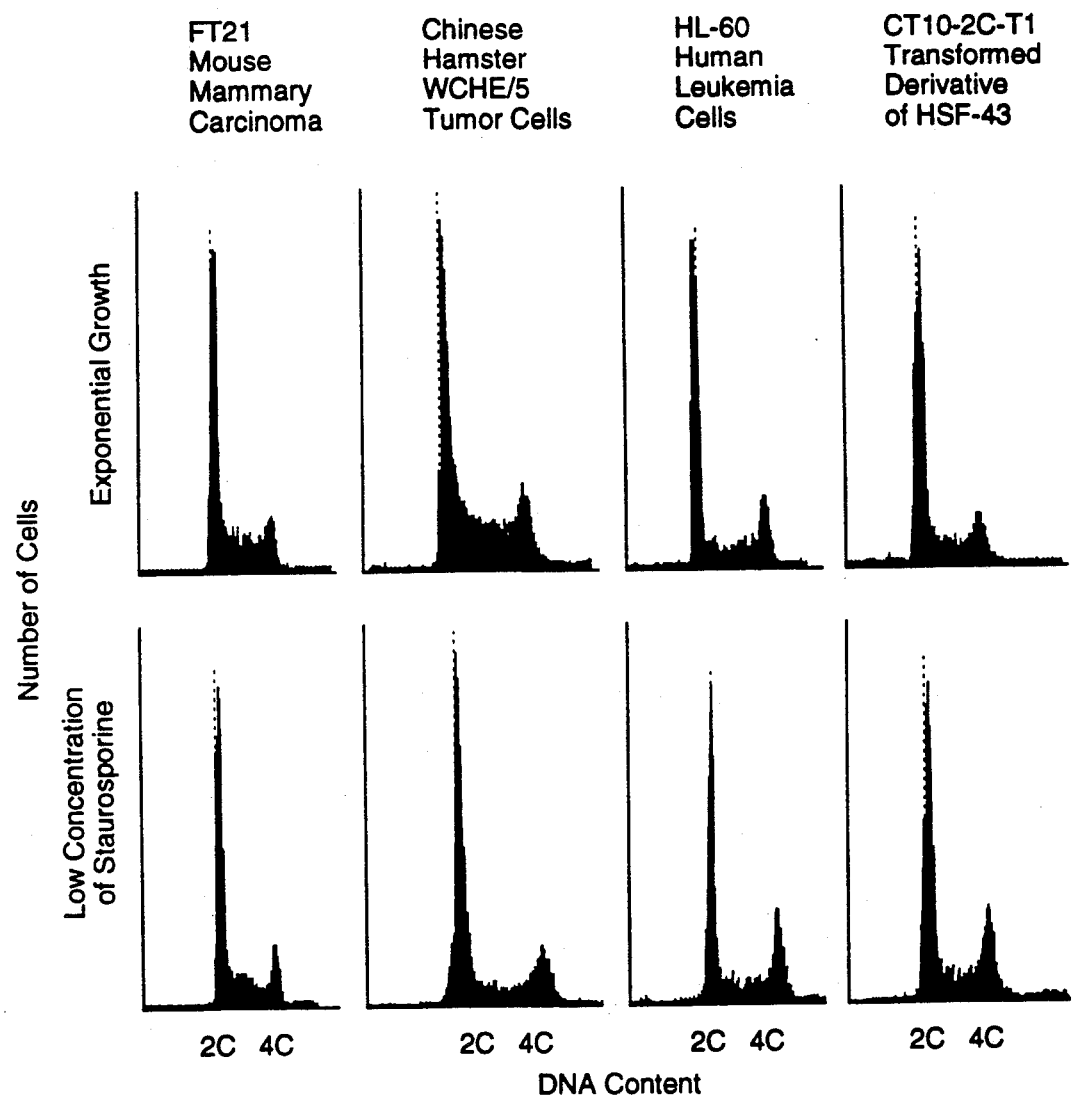

Effect of Staurosporine on Transformed Cells (FIG. 1B

In striking contrast to the results shown in FIG. 1A, staurosporine was unable to arrest transformed cells in $G_0/G_1$. At 10 ng/ml, the drug had no effect on population DNA distribution, as shown in FIG. 1B. Furthermore, the increase in cell number was equivalent to that of the non-drug-treated control, indicating that the cells grew and divided in the presence of the drug rather than undergoing arrest at any stage of the cell cycle.

Figure 2:
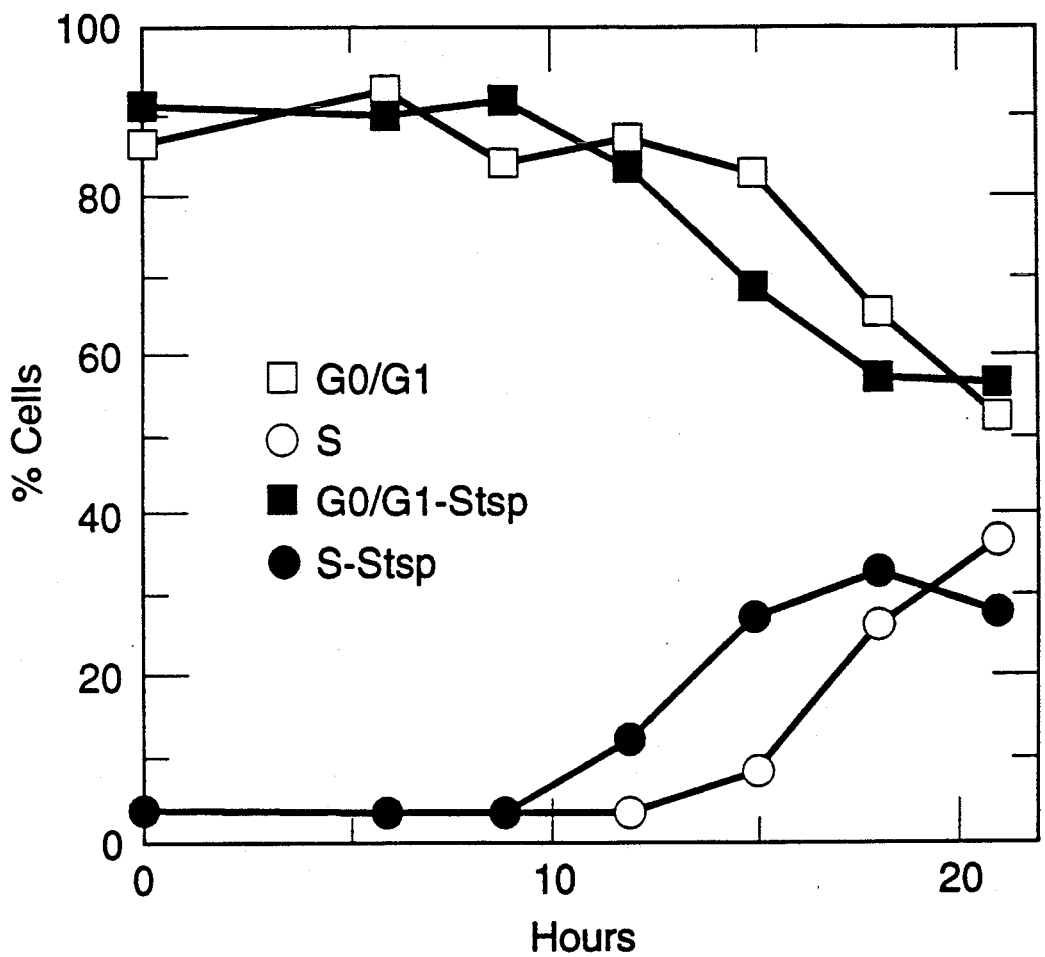
FIG. 2 graphically depicts the recovery kinetics of normal human HSF-43 fibroblasts from a serum-deprived arrest $G_0$ state and a staurosporine arrest $G_1$ state.
Figure 3A:
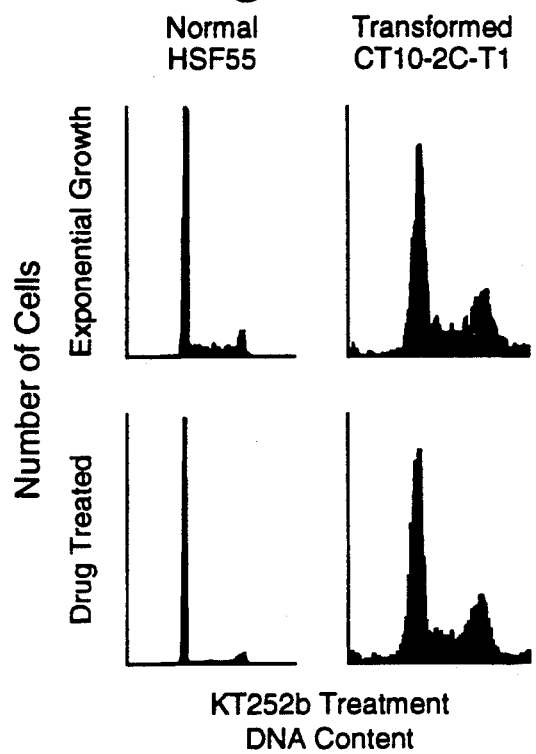
FIGS. 3A, B, C, and D graphically depict the effects of kinase inhibitors K252b, KT5720, KT5823, and KT5926 on normal HSF55 cells and on transformed CT10-2C-T1 cells.
Figure 3B:
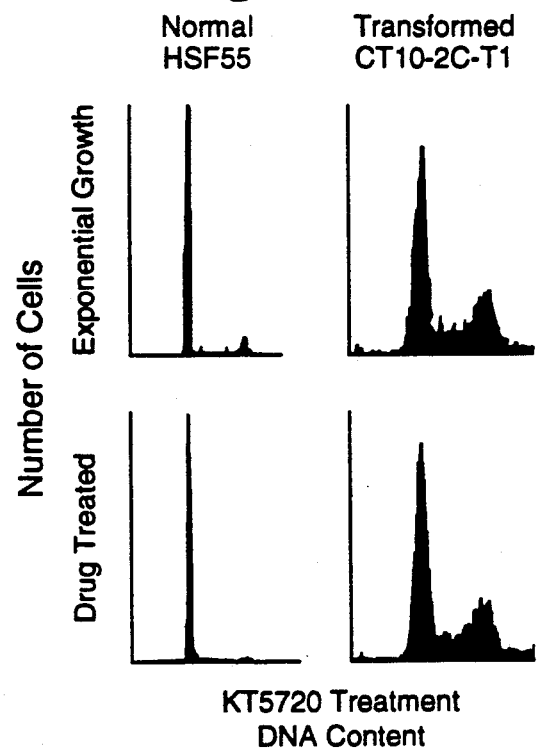
Figure 3C:
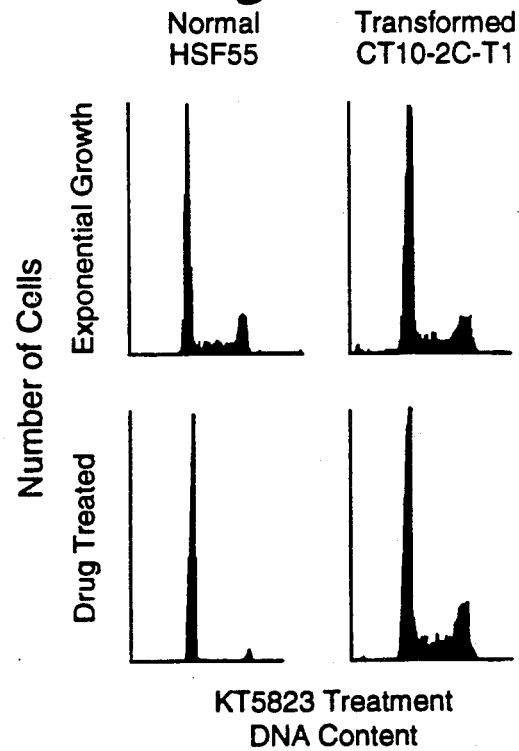
Figure 3D:
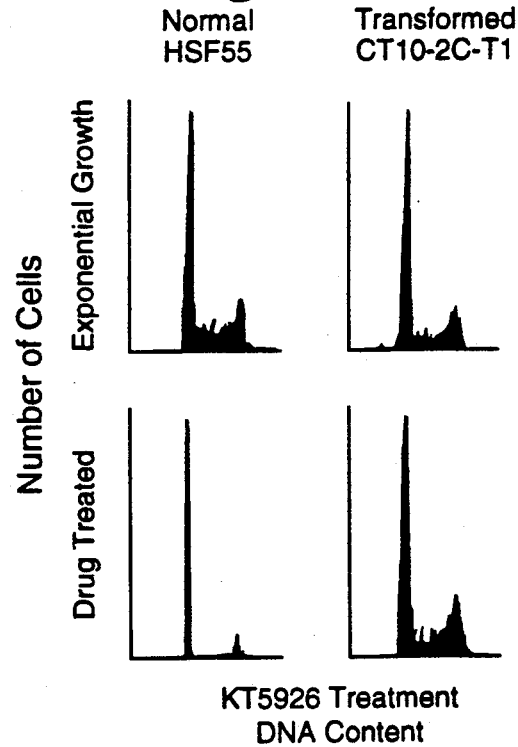

FIG. 2 graphically shows that the effects of staurosporin on mammalian cells are reversible by comparing the kinetics of recovery of normal human HSF43 fibroblasts from a serum-deprived $G_0$ state with recovery from exposure to staurosporine (Stsp) at 10 ng/ml. Initially asynchronous cultures were maintained for 48 hr in $\alpha$MEM/10% BCS to permit them to return to a cycling mode. Asynchronous cultures were exposed to Stsp at 10 ng/ml for 18 hr; at 0 hr, all monolayers were rinsed with phosphate-buffered saline and provided with drug-free complete medium. The increase in S phase cells shows that normal cell cycle has resumed.

In order to demonstrate the general capability of $G_1$ kinase inhibitors to distinguish between normal and transformed cells through arrest of the growth of normal cells in $G_1$, four additional $G_1$ kinase inhibitors were used, identified as K252b, KT5720, KT5823, and KT5926, available from Kimiya Biomedical Company.

The structures of staurosporine and these additional inhibitors are shown below:

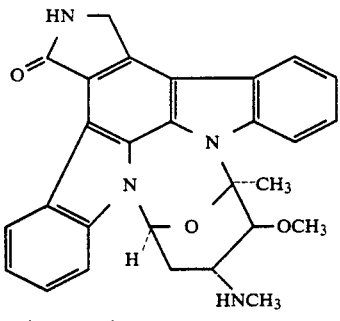

Staurosporine and

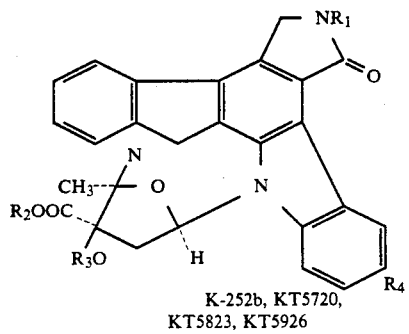

K-252b, KT5720, KT5823, KT5926

|     | K252b | KT5720 | KT5823 | KT5926 |
|-----|-------|--------|--------|--------|
| R₁  | H     | H      | CH₃    | H      |
| R₂  | H     | n-Hex  | CH₃    | CH₃    |
| R₃  | H     | H      | CH₃    | H      |
| R₄  | H     | H      | H      | OCH₂CH₂CH₃ |

These kinase inhibitors were used to treat normal and transformed mammalian cells according to the procedure identified for use with staurosporine. The normal cells used were human diploid fibroblasts, strain 55 (HSF55) and the transformed cells were the CT10-2C-T1 human cell line, identified above. As shown in FIGS. 3A, 3B, 3C, and 3D, all of these kinase inhibitors substantially arrested normal cell growth at $G_0G_1$ and did not affect the transformed cell line. The treatment concentrations are shown in Table A, all in μg/ml and the treatment time was 18 hours.

TABLE A

|           | K252b | KT5720 | KT5823 | KT5926 |
|-----------|-------|--------|--------|--------|
| HSF55     | 5     | 6      | 7.5    | 0.95   |
| CT10-2C-T1| 5     | 6      | 10     | 1      |

Indeed, the transformed cells were treated with concentrations of inhibitor up to 12.5 μg/ml without any accumulation of transformed cells in $G_1$.

FIGS. 4C-4F further show the ability of the normal HSF55 cells to recover from treatment with K252b, KT5720, KT5823, and KT5926 and resume progression in the cell cycle. FIGS. 4A and 4B show the recovery from serum-deprivation arrest and staurosporine arrest for comparison. FIGS. 4B-4F also indicate that the five kinase inhibitors block cells at unique points in $G_1$ but do not affect cell cycle progression of transformed cells.

Figure 5:
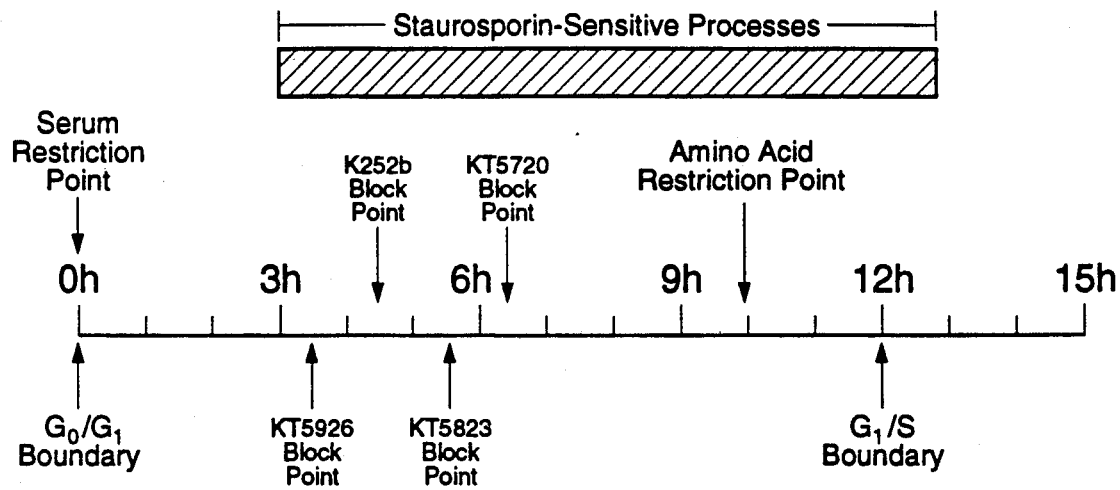
FIG. 5 illustrates the block points and $G_1$ growth cycle sensitivity of HSF55 cells treated with various kinase inhibitors.

FIG. 5 illustrates the progression of cell cycle block points for the above five kinase inhibitors. FIG. 5 also illustrates the sensitivity of normal mammalian cells to staurosporine during most of the $G_1$ phase. This multi-hour period in which staurosporine-sensitive kinases act suggests the existence of a kinase-mediated "$G_1$ clock" mechanism whose continuous operation is essential for progression of cells out of $G_1$. This is further shown by the capability of a wide range of $G_1$ kinase inhibitors to arrest normal mammalian cells in $G_1$.

Thus, a process is provided for selectively growing transformed mammalian cells in a culture containing normal and transformed cells. Treatment of the culture with a low level of a kinase inhibitor, i.e., 1–10 ng/ml of staurosporine, arrests the growth of normal cells in $G_1$ while the growth of the transformed cells continues unabated. This differential growth of transformed cells can then be used to detect transformed cells in patient tissue samples, to detect the presence of transformed cells in a culture of "normal" cells, or to selectively clone transformed cell cultures for research or diagnostic application.

The ability of very low levels of kinase inhibitors, such as staurosporine, to reversibly arrest normal human cells, but not their tumorigenic derivatives, in $G_1$, suggests a role for $G_1$ phase kinase inhibitors as an adjuvant in cancer therapy. The kinase inhibitor may be used to arrest reversibly in $G_1$, and thereby protect, normal tissue cells in cancer patients through the use of a low level of staurosporine that has no effect on the proliferative capabilities of tumor cells. A patient could be treated with a therapeutic regimen with maximum toxicity for actively cycling (i.e., tumor) cells. Far more effective therapeutic doses could be delivered to tumors while simultaneously reducing the harmful side-effects these therapeutic agents produce in normal tissue.

Figure 6:
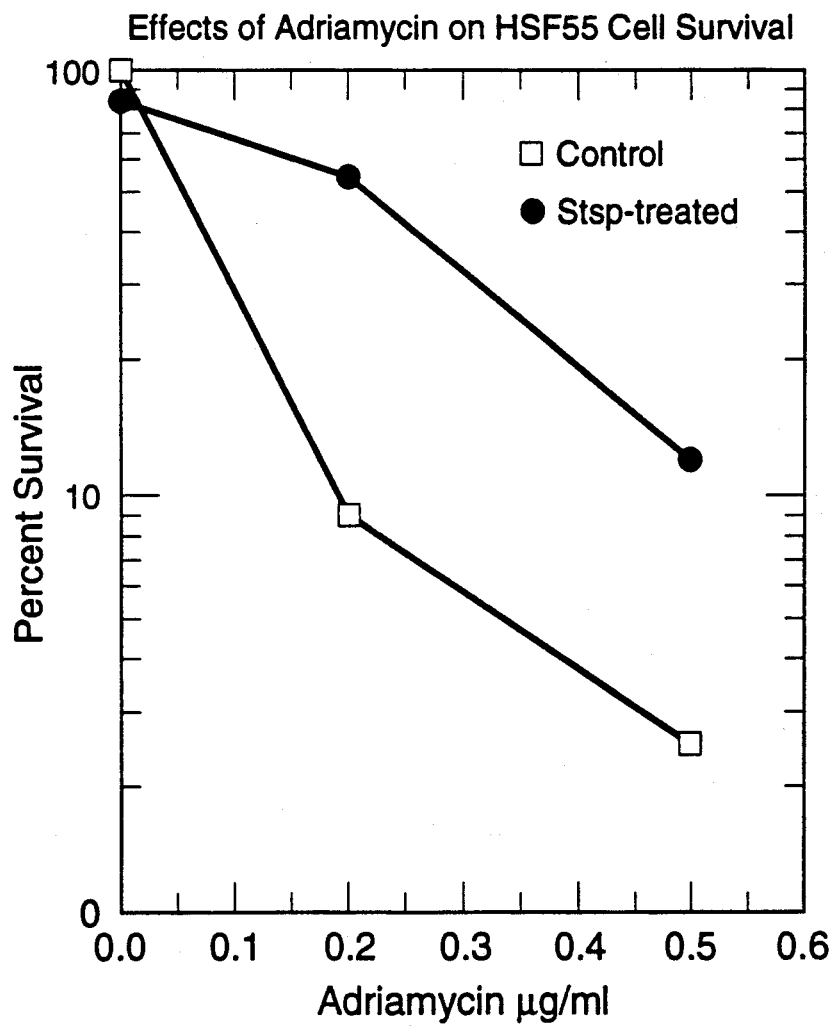
FIG. 6 graphically depicts the survival of normal HSF55 cells treated with a chemotherapeutic agent Adriamycin and illustrates the enhanced survival of cells treated with a kinase inhibitor during application of a chemotherapeutic agent.

This effect is shown in FIG. 6, where HSF55 cells were subjected to treatment with adriamycin, a chemotherapeutic agent, in amounts generally toxic to normal cells. In a control group, the HSF55 cells were not treated with a kinase inhibitor. Another group of HSF55 cells was pretreated with staurosporine in the low concentrations described above. When the adriamycin treatment was complete, the cells were washed and resumption of the cell growth cycle was attempted to determine the survival rate of the cells. FIG. 6 graphically illustrates the greatly enhanced survival rate of the HSF55 cells treated with staurosporine prior to the chemotherapeutic agent.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for distinguishing between normal and transformed mammalian cells, comprising the step of;
   subjecting said normal and transformed cells to low concentrations of a $G_1$ kinase inhibitor effective to arrest said normal cells in $G_1$ without arresting said transformed cells.

2. A method according to claim 1, wherein said kinase inhibitor is staurosporine.

3. A method according to claim 2, wherein said low concentrations are in the range of 1-10 ng/ml.

4. A method according to claim 1, wherein said kinase inhibitor is selected from the group consisting of

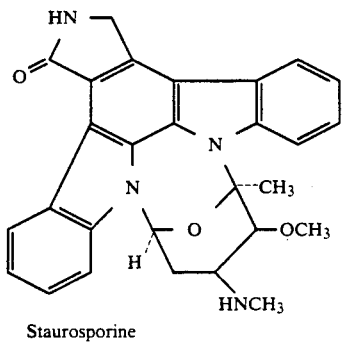
Staurosporine and

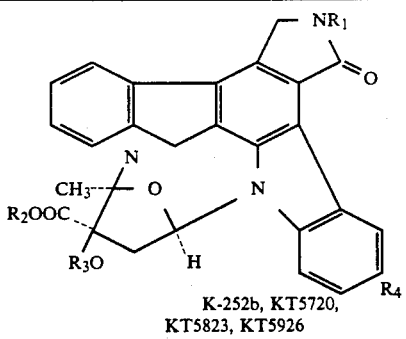
K-252b, KT5720, KT5823, KT5926

|  | K252b | KT5720 | KT5823 | KT5926 |
| --- | --- | --- | --- | --- |
| R1 | H | H | $CH_3$ | H |
| R2 | H | n-Hex | $CH_3$ | $CH_3$ |
| R3 | H | H | $CH_3$ | H |
| R4 | H | H | H | $OCH_2CH_2CH_3$. |

5. A method according to claim 1, further including the steps of:
   growing cultures of said normal and said transformed cells in the presence of said $G_1$ kinase inhibitor; and
   determining the relative growth of cells in said cultures to identify said transformed cells.

6. A method according to claim 2, further including the steps of:
   growing cultures of said normal and said transformed cells in the presence of said $G_1$ kinase inhibitor; and
   determining the relative growth of cells in said cultures to identify said transformed cells.

7. A method according to claim 4, further including the steps of:
   growing cultures of said normal and said transformed cells in the presence of said $G_1$ kinase inhibitor; and
   determining the relative growth of cells in said cultures to identify said transformed cells.

* * * * *